United States Patent [19]
Battenfield

[11] Patent Number: 5,634,904
[45] Date of Patent: Jun. 3, 1997

[54] UNIVERSAL TEMPLATE FOR KNEE INJECTIONS

[76] Inventor: Harold L. Battenfield, 4414 South Zunis, Tulsa, Okla. 74105

[21] Appl. No.: 339,331

[22] Filed: Nov. 14, 1994

Related U.S. Application Data

[63] Continuation-in-part of Ser. No. 145,062, Oct. 26, 1993, Pat. No. 5,364,361.

[51] Int. Cl.$^6$ .................................................. A61M 5/00
[52] U.S. Cl. ........................................ 604/116; 434/272
[58] Field of Search ........................ 604/116; 128/849, 128/850; 434/272, 267, 262

[56] References Cited

U.S. PATENT DOCUMENTS

| | | | |
|---|---|---|---|
| 2,097,039 | 10/1937 | Peterson | 128/347 |
| 2,245,350 | 6/1941 | Marshall | 33/189 |
| 3,542,022 | 11/1970 | Bartnik | 128/2.215 |
| 3,547,121 | 12/1970 | Cherry | 128/215 |
| 3,999,504 | 12/1976 | Kearse | 116/121 |
| 4,228,796 | 10/1980 | Gardiner | 128/215 |
| 4,362,157 | 12/1982 | Keeth | 128/215 |
| 4,733,661 | 3/1988 | Palestrant | 128/303 |
| 4,781,678 | 11/1988 | Couët | 128/215 |
| 4,883,053 | 11/1989 | Simon | 128/303 |
| 5,102,391 | 4/1992 | Palestrant | 604/116 |
| 5,123,907 | 6/1992 | Romaine | 606/131 |

FOREIGN PATENT DOCUMENTS

| 2202445 | 2/1987 | United Kingdom | 604/116 |
|---|---|---|---|

OTHER PUBLICATIONS

Technical Innovations and Notes, Feb. 1984, vol. 10, No. 2.

Primary Examiner—Todd E. Manahan
Attorney, Agent, or Firm—Catalano, Zingerman & Associates

[57] ABSTRACT

The template of this invention includes a flexible sheet with indicia thereon to identify the proper sites and instruction of the proper technique of insertion of an injection device, such as a needle, for medical injection into the human knee. The sheet is flexible so that it may be folded for storage and shipment and then unfolded for placement over the human leg. The template is universal in that it may be used on either the left or right leg on either a male or female patient and may be used on human legs of many different sizes.

12 Claims, 3 Drawing Sheets

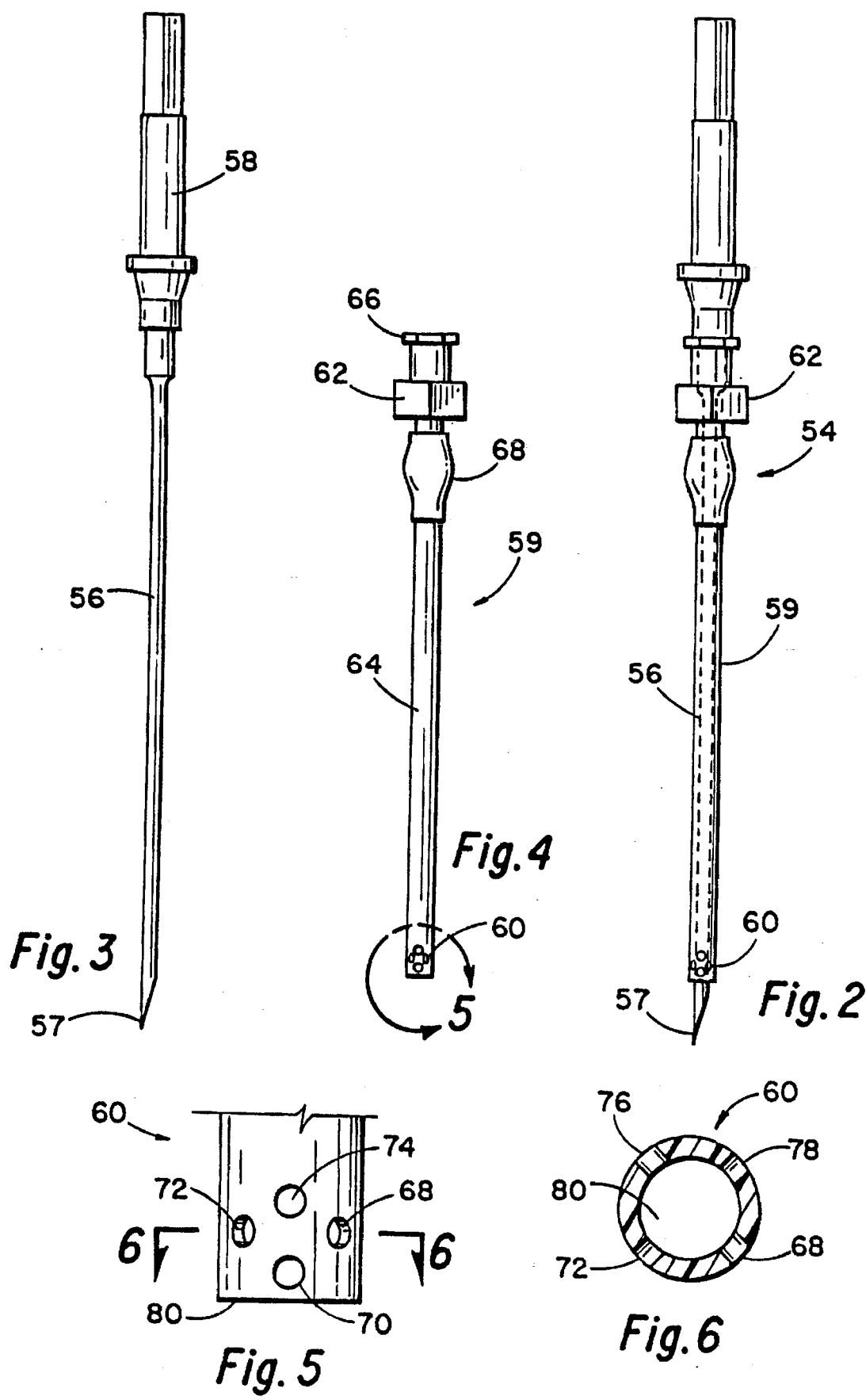

UNIVERSAL TEMPLATE FOR KNEE INJECTIONS

Cross-Reference to Related Application

This application is a continuation-in-part of my application, Serial No. 08/145,062, filed Oct. 26, 1993 now U.S. Pat. No. 5,364,361.

BACKGROUND OF THE INVENTION

1. Field of the Invention

This invention relates to a template and cannulated needle for use in the medical arts to identify proper hypodermic insertion sites and technique, specifically as a guide to identify proper insertion sites and technique for knee injections.

2. Description of the Related Art

Presently there is no known existing apparatus to guide in the medical injection of a human knee. A physician faced with a patient requiring a medical injection in the knee must know the sites on the leg for hypodermic insertion of the injection apparatus in order to properly inject the knee. A need has therefore developed in the medical community for a device which indicates these proper sites and technique.

General Practice or Emergency Room physicians generally have little, or no, training in the proper technique or a location of insertion of injection apparatus for injection into the knee of a patient. Presently, a needle is the commonly used apparatus for administering medical injections into the human knee. It is often not known where around the perimeter of the patella the needle should be inserted, to what depth, or at what angle. This uncertainty causes attempts to inject at various improper locations which are ineffective and cause extreme discomfort to the patient. Under the present system in medical schools, there is no practical method of teaching physicians in training the proper sites and techniques of insertion of a needle for injection into the knee. In training, medical students frequently learn anatomy from cadavers. Injection of the knee is carried out with the patient sitting in the upright position and the knees bent at 90°. This position is impossible with a cadaver which is very stiff and unyielding. Therefore, proper injection techniques and locations are generally not practiced. In addition, body fluids are drained from cadavers, which renders the experience much different than with a live patient in a clinical setting. The only way to properly learn is on a patient who is awake who would experience the pain and discomfort from the procedure. Generally, therefore, the technique for proper injection into the knee is taught by demonstration by an experienced physician rather than hands-on training by the student. Consequently, trained physicians frequently have little knowledge of the proper sites, the best technique, or proper angles of insertion of a needle for injection into the knee of a patient.

SUMMARY OF THE INVENTION

The template of this invention is constructed of flexible material so that it may be folded for packaging, transport, and storage and then unfolded for use. Indicia are contained on the template for locating it on a human leg over the knee area. This locating indicia includes patella indicium and tibia indicium which are placed over the patella and tibia, respectively, of the patient's leg. The template is universal in that it may be used on either the left or right leg on either a male or female patient and may be used on human legs of many different sizes.

Insertion indicia on the template identify the proper sites and angles of inserting the device used for hypodermic injection into the knee of the patient. The insertion indicia are placed on the template such that when the patella and tibia indicia are overlaid upon the patella and tibia of the leg, the insertion indicia will overlay the proper insertion sites. The insertion indicia also include instruction of the proper angle of hypodermic insertion of an injection device into the patient's knee.

A plan view diagram may be placed on the template illustrating the template properly draped over the knee area of the human leg. The plan view diagram illustrates the proper sites of hypodermic insertion of the device used for injection into the knee of a patient, as well as illustrates the proper horizontal angle of insertion of the injection device in relation to the patient's leg anatomy.

A lateral view diagram may also be placed on the template which illustrates the proper site and vertical angle of insertion of the injection device into the patient's knee. A cut-away of a human leg is depicted with its femur, tibia, tendons (in phantom), and patella illustrated. The injection device is shown inserted into the knee as it is bent with the femur being 90° from the tibia. The injection device is shown inserted at the proper location and angle as instructed by the template.

It is therefore an object of this invention to describe a template used to instruct proper sites and technique for injection into the knee of a human leg. The template solves the problem of lack of previous medical training in that it fully depicts and instructs the proper location and technique for injection into a patient's knee without the requirement of outside instruction so that it may be used in a private office setting without a learning curve.

BRIEF DESCRIPTION OF THE DRAWINGS

FIG. 2 is a side elevational view of the cannulated needle for use with the template of this invention.

FIG. 3 is a side elevational view of the rigid needle of the cannulated needle of FIG. 2.

FIG. 4 is a side elevational view of the cannula of the cannulated needle of FIG. 2.

FIG. 5 is an enlarged view of section 5 of FIG. 4.

FIG. 6 is a view taken along the line 6—6 of FIG. 5.

DETAILED DESCRIPTION OF THE PREFERRED EMBODIMENT

Figure 1:
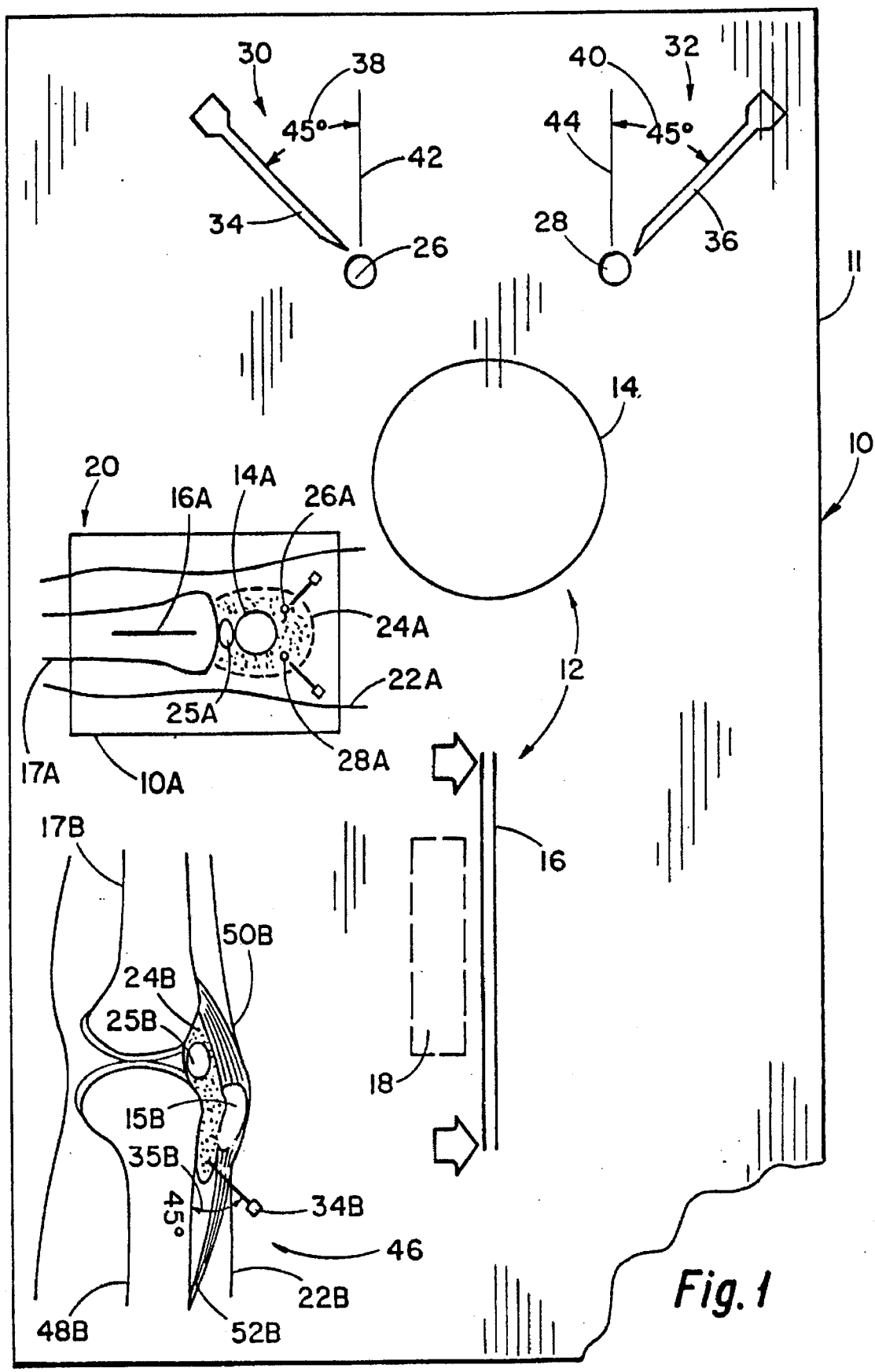
FIG. 1 is a top plan view of the template of this invention.

The drawings represent the present invention wherein FIG. 1 shows a top plan view of the preferred embodiment of the template of this invention, generally 10. Template 10 may be constructed from any suitable flexible sheet of material 11 so that it may be folded for packaging and transport and then later unfolded and draped over a patient's leg for use. Template 10 is universal as it may be used on either a right or left knee regardless of the size of the patient and has indicia thereon for locating it on a human leg over a patient's knee. Template 10 has indicia thereon for locating it on a human leg over a patient's knee, patella indicium 14 and tibia indicium 16. Patella indicium 14 is circular to illustrate the patella of the knee of a human leg. Tibia indicium 16 is defined by a pair of parallel lines used to orient template 10 over the leg. Tibia indicium 16 also includes tibia alignment instructions 18 so that the user of template 10 knows to align tibia indicium 16 on the crest of the tibia of the human leg.

Template 10 also includes insertion indicia 26 and 28. Insertion indicia 26 and 28 are holes cut in the template to identify the proper sites for hypodermic insertion of a device to drain a bursa of the knee which is filled with fluid, or distended.

Template 10 may also include a plan view diagram, generally 20, illustrating template 10 draped over a human leg. For the purpose of clarity in this description, reference numerals on plan view diagram 20 are the same as the reference numerals used in the general description of template 10 designating like elements. Like elements on plan view diagram 20, however, are distinguished by the letter "A".

Plan view diagram 20 depicts template 10A as it is properly placed over human leg 22 having a distended bursa 24A. A diagram such as plan view diagram 20 may be placed on template 10 for instructional purposes, or it may be placed on printed material which would accompany template 10.

Patella indicium 14A is overlaid upon the patella (not shown in plan view diagram 20) of the patient's knee. Likewise, tibia indicium 16A is overlaid upon the crest of the tibia 17A of leg 22A. When patella indicium 14A and tibia indicium 16A are properly overlaid upon the corresponding anatomical features of leg 22A (the patella and tibia 17A), insertion indicia 26A and 28A identify the proper sites for insertion of the device to drain distended bursa 24A.

As seen on plan view 20, 26A and 28A are the proper sites for insertion of a drainage device because of the presence of a fat pad 25A located below patella 14A. If a drainage device, such as a needle, were to be inserted at the point of fat pad 25A and fluid drained, the fat pad would be drawn to and block the end of the needle. This is the same principle upon which a ball valve operates, thereby preventing any further fluid drainage.

Once the proper sites for insertion, as identified by insertion indicia 26 and 28, are located, the draining device may be inserted at either point 26 or 28. In order to instruct proper angular insertion of the draining device, angular indicia 30 and 32 are placed on template 10. Angular indicia 30 and 32 include illustrations of draining devices 34 and 36, angular instructions 38 and 40, and reference lines 42 and 44. Angular indicia 30 and 32 instruct the physician that the proper angle for insertion of a drainage device, either 34 or 36, is 45½ (or the proper angle instructed as 38 or 40) from its corresponding reference line 42 or 44. As illustrated in FIG. 1, the proper angle of insertion of needle 34 is 45½ toward patella 14 from reference line 42.

Template 10 may also include lateral view diagram 46. For the purposes of clarity in this description, reference numerals on lateral view diagram 46 are the same as the reference numerals used in the general description of template 10, distinguished by the letter "B", to describe like elements. Lateral view diagram 46 is a lateral cut-away of leg 22B depicting the proper point and angle of insertion of draining device 34B. Lateral view diagram 46 illustrates tibia 17B, femur 48B, patella 15B, tendons generally 50B and 52B, and distended bursa 24B. Draining device 34B is properly inserted in lateral view diagram 46 such that it is inserted into leg 22B through tendon 52B at the proper angle instructed by template 10.

A second angular indicium 35B instructs the proper angle of insertion of the draining device 34B in relation to femur 48B. As can be seen on lateral view diagram 46, draining device 34B is inserted at a 45I angle from femur 48B.

Draining device 34B is shown entering distended bursa 24B in order for distended bursa 24B to be drained of fluid. It is understood that a diagram, such as lateral view diagram 46, may be placed on template 10 or may be included with printed material which would accompany template 10 for instructional purposes.

FIG. 2 depicts the cannulated needle 54 of this invention for insertion into, and draining of, a distended bursa. Cannulated needle 54 is particularly suited for use with template 10 of FIG. 1 to drain a distended knee bursa as described herein. It is understood, however, that cannulated needle 54 is useful for drainage of bursa other than knee bursa.

Cannulated needle 54 includes a rigid needle 56 and cannula 59. Rigid needle 56, as shown partially in phantom in FIG. 2, is inserted the length of cannula 59. Cannula 59 has a leading end 60 and a trailing end 62. The leading end 60 of cannula 59 contains a plurality of apertures therein.

In use, cannulated needle 54 is inserted at the proper site and angle of the patient's leg as identified by template 10 of FIG. 1. Point 57 of rigid needle 56 extends beyond cannula 59 and is sharpened to facilitate insertion. Once cannulated needle 54 is inserted into the leg at the proper site and angle, leading end 60 of cannula 59 is inserted into the fluid in the bursa. Rigid needle 56 is then withdrawn from cannula 59, leaving cannula 59 inserted in the bursa. A hypodermic syringe (not shown) is attached to trailing end 62 of cannula 59. Fluid is then drained from the bursa through cannula 59 into the barrel of the syringe by the vacuum created from withdrawing the syringe plunger.

FIG. 3 depicts rigid needle 56 removed from the cannula. Rigid needle 56 includes point 57 and hub 58. As stated, point 57 facilitates penetration of needle 56 into the distended bursa. Hub 58 is designed on one end to insert into the locking tip on the barrel of a hypodermic syringe and on its other end into the trailing end 62 (of FIG. 3) of cannula 59. Hub 58 is of a length so as to be held by the physician for insertion into the leg in the event insertion into a hypodermic syringe is not desired. Rigid needle 56 is tubular in order to allow drainage of fluid without withdrawing it from the cannula.

FIG. 4 shows cannula 59 with rigid needle 56 of FIG. 2 removed. Cannula 59 is made up of leading end 60, body 64, and trailing end 62. Trailing end 62 includes an adapter 66 into which either needle hub 58 of FIG. 3 or the locking tip of a hypodermic syringe is fit. A flexible member 68 connects cannula 64 with adapter 66.

The procedure of inserting a draining device and draining a knee bursa of fluid can cause a great amount of discomfort to the patient because of blind probing into the bursa walls with the sharp needle point. Body 64 of cannula 59 of the present invention is flexible so that as the bursa is being ndrained of fluid, body 64 can be manipulated within the bursa to access the greatest amount of fluid without being overly invasive.

FIG. 5 is an enlarged view of leading end 60, section 5 of FIG. 4. Leading end 60 is blunt so that as the bursa contracts from fluid being drained, leading end 60 will not stick into the bursa inner wall if contact is made.

Leading end 60 contains a plurality of apertures, or holes, 68, 70, 72, and 74. FIG. 6 is a cross-sectional view taken along line 6-6 of FIG. 5 showing that apertures 68, 72, 76, and 78 are drilled completely through wall 80 of leading end 60. Apertures 68, 72, 76, and 78 may be drilled around the circumference of circular leading end 60.

Referring back to FIG. 5, if the open end 80 of circular leading end 60 becomes blocked by contact with the inner wall of the bursa or clogged by solid material in the fluid, drainage of the bursa can be maintained through apertures 68, 70, 72, and 74. Likewise, if aperture 68 becomes blocked or clogged, fluid can still drain through apertures 70, 72, 74, and the open end 80. It should be understood that the number of apertures in circular leading end 60 could vary as required. In addition, the placement or shape of these apertures should not be limited by this description or the accompanying drawings. Any number of suitable shapes or placement or apertures could be employed to prevent complete clogging or blockage of leading end 60.

Figure 7:
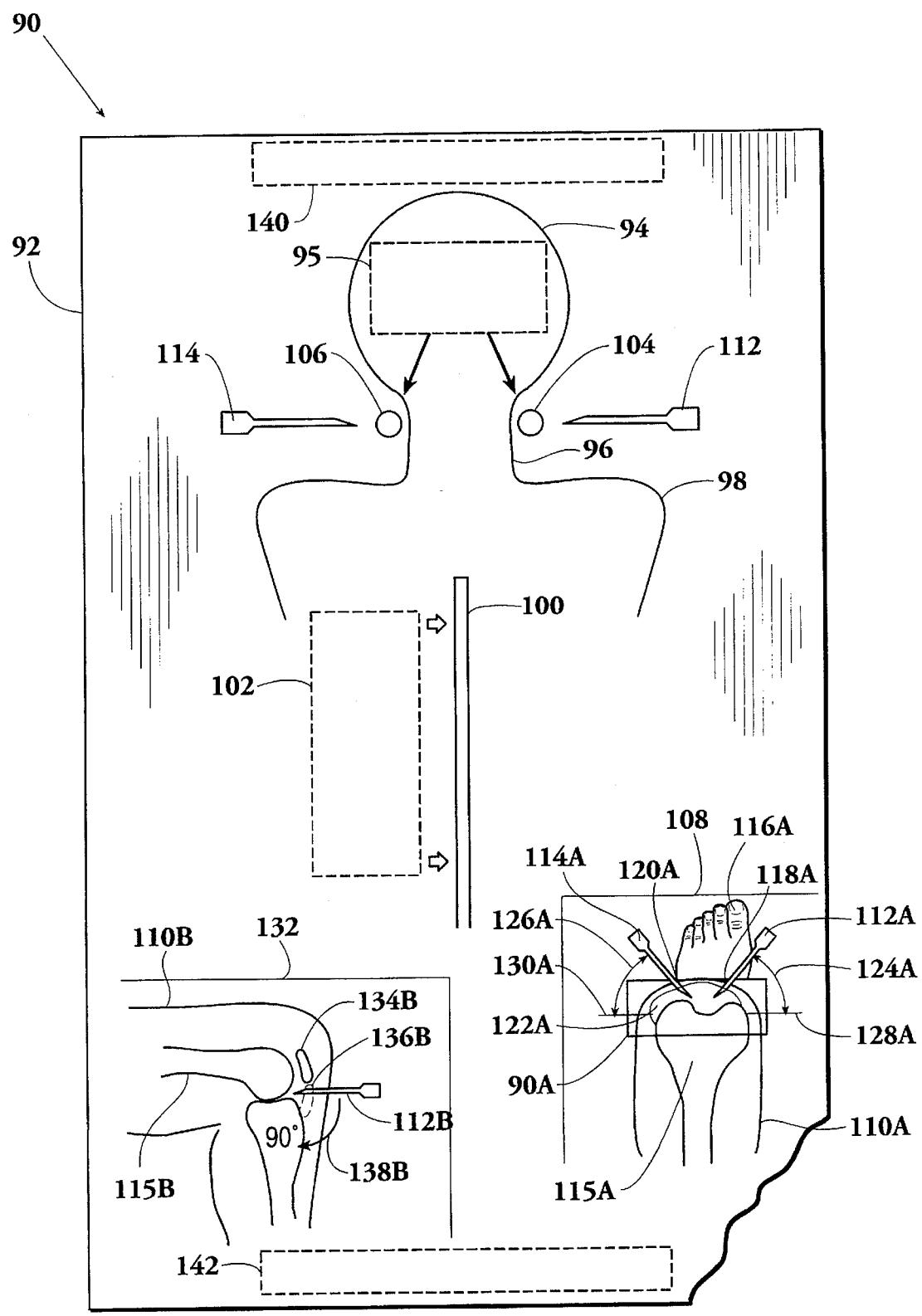
FIG. 7 is a top plan view of the template of this invention for instruction of the proper sites and techniques for insertion of an injection device into a human knee.

FIG. 7 shows a top plan view of the template of this invention for instruction of proper sites and techniques for the insertion of a medical injection device into a skeletal joint, and particularly, a human knee. Template 90 may be constructed from any suitable, flexible sheet of material 92 so that it may be folded for packaging, transport, and storage and then later unfolded and draped over a patient's leg for use. Template 90 is universal as it may be used on either a right or left knee of either a male or female, regardless of the size of the patient and has indicia thereon for locating it on a human leg over a patient's knee. Template 90 has indicia thereon for locating it on a human leg which include patella indicium 94, tendon indicia 96, and tibia indicia 98 and 100. Patella indicium 94 is substantially circular to illustrate the patella of the knee of the human leg. Patella indicium 94 also includes patella alignment instructions 95 so that the user of template 90 is instructed to align the lower circumference of patella indicium 94 with the inferior border of the patient's patella. Tendon indicium 96 extends from the lower circumference of patella indicium 94 and illustrates the patella tendon which extends from the patella to the tibia. Tibia indicia 98 illustrates the upper portion of the tibia plateau to which the patella tendon is attached. Tibia indicium 100 is defined by a pair of parallel lines used to orient template 90 over the patient's leg. Tibia indicium 100 also includes tibia alignment instructions 102 so that the user of template 90 is instructed to align tibia indicium 100 on the crest of the tibia of the leg.

In use, patella indicium 94, tendon indicium 96, and tibia indicia 98 and 100 are overlaid upon their corresponding anatomies of the patient's leg in order to identify the proper sites 104 and 106 of injection into the patient's knee.

Template 90 also includes insertion indicia 104 and 106. Insertion indicia 104 and 106 in the preferred embodiment are holes cut in the template to identify the proper sites for hypodermic insertion of a device for medical injection into the skeletal joint.

Template 90 may include a top plan view diagram, generally 108, illustrating template 90 draped over the knee area of a human leg. For the purpose of clarity in this description, reference numerals on plan view diagram 108 are the same as the reference numerals used in the general description of template 90 designating like elements. Like elements in plan view diagram 108, however, are distinguished by the letter "A".

Top plan view diagram 108 depicts template 90A as it is properly placed over human leg 110A. A diagram such as plan view diagram 108 may be placed on template 90 for instructional purposes, or it may be placed on printed material which would accompany template 90.

As shown in top plan view diagram 108, when inserting an injection device, such as is depicted by needle indicia 112A and 114A, the patient is generally in a sitting position with the knee bent so that the femur 115A and tibia 122A are substantially 90° from one another and foot 116A is either parallel to or resting on the floor.

Top plan view 108 depicts the left leg of the patient. It is understood that a drawing depicting a right foot could be inserted for foot 116A. It is further understood that template 90 could be used on a patient's right leg even though top plan view 108 depicts a left leg. Template 90 would still identify the proper injection sites and injection technique.

Patella indicium 94A is overlaid upon the patella (not shown in plan view diagram 108) of the patient's knee. Likewise, tibia indicium 100A (not shown) is overlaid upon the crest of the patient's tibia and tibia indicium 98 overlays the upper portion of the patient's tibia 122A of leg 110A. When patella indicium 94A, tendon indicium 96A, and tibia indicia 98 and 100 are properly overlaid upon the corresponding anatomical features of leg 110A (the patella and tibia 122A), insertion indicia 118A and 120A identify the proper sites for insertion of an injection device into leg 110A.

In order to instruct proper angular insertion of the injection device, angular indicia 124A and 126A are included in top plan view 108 of template 90. Angular indicia 124A and 126A include illustrations of draining devices 112A and 114A and reference lines 128A and 130A. Angular indicia 124A and 126A instruct the physician that the injection device 112A should be inserted at an angular of 45° from reference line 120A, on the same horizontal plane. Likewise, injection device 114A should be inserted at an angle of 45° from reference line 130A on the same horizontal plane. As illustrated in top plan view 108, the proper angle of insertion of needle 112A is 45° toward foot 116A from reference line 128A on a horizontal plane parallel to foot 116A. Likewise, needle 114A is injected at a 45° angle toward foot 116A from reference line 130A on a horizontal plane parallel to foot 116A.

An insertion device such as needle 112 or needle 114 should properly be inserted on either side of the patella tendon 96 so as not to perforate this tendon 96. Needle 112 or needle 114 should be inserted at approximately a 45° angle so as to extend under this patella tendon 96 and into the bursa of the knee. Either needle 112 and 114 is properly inserted in the space between patella 94 and tibia 98. Insertion sites 104 and 106 are the proper sites for insertion of an injection device because of the presence of a fat pad located below the patella. If an insertion device, such as a needle, were to be inserted at the point of the fat pad, the needle would not properly extend into the knee bursa and the material to be injected would be injected inside the fat pads, reducing its effectiveness and causing great discomfort to the patient.

Template 90 may also include lateral view diagram 132. For the purposes of clarity in this description, reference numerals on lateral view diagram 132 are the same as the reference numerals used in the general description of template 90 and top plan view 108, distinguished by the letter "B" to describe like elements. Lateral view diagram 132 is a lateral cut-away view of leg 110B depicting the proper site and angle of insertion of injection device 112B. Lateral view diagram 132 illustrates femur 115B, tibia 122B, patella 134B, and patella tendon 136B. Injection device 112B is properly inserted in lateral view diagram 132 such that it is inserted into leg 110B between patella 134B and tibia 122B.

A second angular indicium1BSB instructs the proper angle of insertion of injection device 112B in relation to tibia 122B. As can be seen on lateral view diagram 132, injection device 112B is inserted at a 90° angle from tibia 122B, or parallel to the floor, assuming that the floor is level. Injection device 112B is also inserted parallel to femur 115B but extending opposite femur 115B.

It is understood that a diagram, such as lateral view diagram 132, may be placed on template 90 or may be included with printed material which would accompany template 90. Since template 90 is used on a bent knee, adhesive strips 140 and 142 will be applied to template 90 so as to secure template 90 over the patient's knee. Otherwise, gravity may cause template 90 to fall off the knee during use.

While the drawings and preferred embodiments relate to templates for identifying sites of insertion of devices for either draining or injection into the human knee, it is understood that a template could be directed by one skilled in the art to any skeletal joint by including the relevant anatomy for the particular joint. It is further understood that the invention is not restricted to skeletal joints of humans but could be directed by one skilled in the art to skeletal joints of animals as well.

It is yet further understood that the invention is not restricted to means to drain a distended bursa or injection means but could be used with any device for hypodermic insertion into a skeletal joint.

While the invention has been described with a certain degree of particularity, it is manifest that many changes may be made in the details of construction without departing from the spirit and scope of this disclosure. It is understood that the invention is not limited to the embodiment set forth herein for purposes of exemplification, but is to be limited only by the scope of the attached claim or claims, including the full range of equivalency to which each element thereof is entitled.

What is claimed is:

1. A template for instructing proper insertion of a hypodermic injection device into a skeletal joint located on the human anatomy, comprising:

a flexible sheet;

means for locating said flexible sheet on a particular portion of the anatomy;

means for identifying proper insertion of the hypodermic injection device into said skeletal joint;

indicia on said flexible sheet illustrating anatomical features so that the flexible sheet may be overlaid upon the anatomy.

2. The template of claim 1 wherein said means for locating said flexible sheet also includes at least one diagram of the anatomy with the template thereon.

3. The template of claim 1 wherein said means for identifying proper insertion of the injection device includes:

indicia on said flexible sheet illustrating proper sites of insertion of the hypodermic device such that when said indicia illustrating anatomical features are overlaid upon the anatomy, said indicia illustrating proper sites of insertion of the hypodermic device will overlay the proper sites on the anatomy for insertion of the hypodermic device.

4. The template of claim 3 wherein said means for identifying proper insertion of the hypodermic device also includes indicia on said flexible sheet illustrating proper angles of insertion of the hypodermic device.

5. A template for instructing proper hypodermic injection into a human knee, comprising:

a flexible sheet;

indicia on said flexible sheet illustrating anatomical features of the human leg so that the flexible sheet may be overlaid upon the leg;

means for identifying proper insertion of a hypodermic injection device.

6. The template of claim 5 further including at least one diagram of the human leg with the template thereon.

7. The template of claim 5 wherein said means for identifying proper insertion of a hypodermic injection device includes:

Indicia on said flexible sheet illustrating proper sites of insertion of the hypodermic injection device such that when said indicia illustrating anatomical features of the human leg are overlaid upon the leg, said indicia illustrating proper sites of insertion of the hypodermic injection device will overlay the proper sites on the leg for insertion of the hypodermic injection device.

8. The template of claim 7 further including indicia on said flexible sheet illustrating the proper angles of insertion of the hypodermic injection device.

9. An apparatus for identifying a set of sites for proper hypodermic insertion of a needle into the knee of a human leg having a patella and tibia, comprising:

a flexible template;

a first set of indicia on said flexible template illustrating the patella and tibia so that said first set of indicia may be overlaid upon the patella and tibia of the human leg;

a second set of indicia on said flexible template illustrating proper sites and angles of insertion of said needle into the knee such that when said first set of indicia are overlaid upon the human leg, said second set of indicia overlay the proper sites on the leg for insertion of said needle.

10. The apparatus of claim 9 including at least one plan view diagram on said template illustrating the human leg with the template properly overlaid thereon and said needle inseded into said knee at a proper site and angle.

11. The apparatus of claim 9 including at least one lateral view diagram on said template illustrating the human leg with the template properly overlaid thereon.

12. The apparatus of claim 9 including at least one adhesive strip to removably secure said template to said human leg.

* * * * *